(12) United States Patent
Poupin

(10) Patent No.: US 9,040,240 B2
(45) Date of Patent: May 26, 2015

(54) ARSENIC ASSAY USING ELISA

(75) Inventor: Pascal Poupin, Metz (FR)

(73) Assignee: UNIVERSITE DE LORRAINE (FR)

( * ) Notice: Subject to any disclaimer, the term of this patent is extended or adjusted under 35 U.S.C. 154(b) by 46 days.

(21) Appl. No.: 14/001,648

(22) PCT Filed: Feb. 23, 2012

(86) PCT No.: PCT/FR2012/050377
§ 371 (c)(1),
(2), (4) Date: Aug. 26, 2013

(87) PCT Pub. No.: WO2012/114046
PCT Pub. Date: Aug. 30, 2012

(65) Prior Publication Data
US 2013/0337464 A1    Dec. 19, 2013

(30) Foreign Application Priority Data
Feb. 25, 2011    (FR) ..................................... 11 51566

(51) Int. Cl.
*C12Q 1/68* (2006.01)
*G01N 33/53* (2006.01)
*G01N 33/84* (2006.01)

(52) U.S. Cl.
CPC *C12Q 1/689* (2013.01); *C12Q 1/68* (2013.01); *C12Q 1/6834* (2013.01); *G01N 33/53* (2013.01); *G01N 33/84* (2013.01)

(58) Field of Classification Search
None
See application file for complete search history.

(56) References Cited

U.S. PATENT DOCUMENTS

| 5,459,040 A | 10/1995 | Hammock et al. |
| 2003/0096275 A1 | 5/2003 | Laing |
| 2003/0109451 A1 | 6/2003 | Hillman et al. |

FOREIGN PATENT DOCUMENTS

| WO | 8502412 A1 | 6/1985 |
| WO | 9519446 A1 | 7/1995 |
| WO | 03062786 A2 | 7/2003 |
| WO | 03102223 A1 | 12/2003 |
| WO | 2007073163 A1 | 6/2007 |
| WO | 2008103350 A1 | 8/2008 |
| WO | 2010004736 A1 | 1/2010 |
| WO | 2010092539 A1 | 8/2010 |

OTHER PUBLICATIONS

International Search Report issued Jun. 6, 2012 re: PCT/FR2012/050377; citing: WO 2010/004736 A1, US 2003/096275 A1, Kawakami et al. "Application of flourescent", Stocker et al. "Development of a set", and US 5,459,040 A.

Yasunari Kawakami et al. "Application of flourescent protein-tagged trans factors and immobilized cis elements to monitoring of toxic metals based on in vitro protein-DNA interactions", Biosensors and Bioelectronics, Dec. 15, 2010, pp. 1466-1473; vol. 26, No. 4, XP027546866.
Judith Stocker, et al. "Development of a Set of Simple Bacterial Biosensors for Quantitative and Rapid Measurements of Arsenite and Arsenate in Potable Water", Environmental Science & Technology, Oct. 15, 2003, pp. 4743-4750, vol. 37, No. 20, XP002449112.
Weng C. Chan et al. "FMOC Solid Phase Peptide Synthesis: A Practical Approach"; Oxford Univ Press OUP Oxford ; 2000; abstract.
Francoise Cordier-Ochsenbein et al. "Exploring the Folding Pathways of Annexin I, a Multidomain Protein. II. Hierarchy in Domain Folding Propensities may Govern the Foldng Process"; J. Mol. Biol.; Article No. mb981828; 1998; vol. 279; pp. 1177-1185.
John R. Crowther "Elisa: Theory and Practice (Methods in Molecular Biology)"; 1995; Vol. 42; Part 1; pp. 35-61; 10.1385/0-89603-279-5:35; abstract.
"Reduction of Arsenic Safety and Groundwater"; Organisation Mondiale de la Sante EB118-14; May 24, 2006; 5 pages.
E. Harlow et al. "Protocols for preparing immunogens, immunization of animals, and collection of antiserum may be found in Antibodies: A Laboratory Manual"; Cold Spring Harbor Laboratory; 1988; pp. 55-120.
Dang Q. Hung et al. "Analytical methods for inoraganice arsenic in water: a review"; Talanta; 2004; vol. 64; pp. 269-277.
Jan-Christer Janson "Principles, High Resolution Methods, and Applications"; Protein Purification; Third Edition, John Wiley & Sons, Inc.; 2011; 20 pages.
Bruno Miroux et al. "Over-production of Proteins in *Escherichia coli*: Mutan Hosts that Allow Synthesis of some Membrane Proteins and Globular Proteins at Hight Levels"; J. Mol. Biol.; 1996; vol. 260; pp. 289-298.
Rita Mukhopadhyay et al. "Microbial arsenic: from geocycles to genes and enzymes"; FEMS Microbiology Reviews; 2002; vol. 26; pp. 311-325.
The QiaExpressionist : A handbook for high-level expression and purification of 6xHis-tagged proteins. Jun. 2003. Fifth ed., Qiagen.
Alan H. Rosenberg et al. "Vector for selective expression of cloned DNAs by T7 RNA polymerase"; Gene; 1987; vol. 56; pp. 125-135.
Jacob Sagiv "Organized Monolayers by Adsorption. 1. Formation and Structure of Oleophobic Mixed Monolayers on Solid Surface"; Journal of the American Chemical Society; Jan. 2, 1980; vol. 102; No. 1; pp. 92-98.

(Continued)

*Primary Examiner* — James Martinell
(74) *Attorney, Agent, or Firm* — Cantor Colburn LLP

(57) ABSTRACT

The invention relates to a process involving analyzing the presence of arsenic in a sample, comprising the following steps:
  (a) contacting a sample suspected of containing arsenic on a solid support functionalized with a DNA fragment comprising an ArsR protein binding site, site on which an ArsR protein is attached, the presence arsenic causing separation of the ArsR protein from the DNA fragment;
  (b) incubation of the sample in contact with the said support;
  (c) elimination of ArsR protein separated from the DNA fragment by washing the support after the incubation carried out in step (b); and
  (d) analyzing by an ELISA technique to detect the presence or absence of ArsR protein remaining attached to the DNA fragment.

15 Claims, 3 Drawing Sheets

(56) References Cited

OTHER PUBLICATIONS

Michael A. Sorensen et al. "Codon Usage Determines Translation Rate in *Escherichia coli*"; Jol. Mol. Biol.; 1989; vol. 207; pp. 365-377.

Abstract of TW200525147A; "Process for Detecting Arsenic and Reagents Thereof"; Aug. 2005; abstract.

J.R. Van Der Meer "Bacterial Biosensors for the Detection of Arsenic in Drinking Water"; EAWAG News; vol. 56; pp. 12-14.

Chun Xu et al. "Dimerization is Essential for DNA Binding and Repression by the ArsR Metalloregulatory Protein of *Escherichia coli*"; The Journal of Biological Chemistry; Jun. 20, 1997; vol. 272; No. 25; pp. 15734-15378.

Shiping Zhang et al. "Low-usage codons in *Escherichia coli*, yeast, fruit fly and primates"; Gene; 1991; vol. 105; pp. 61-72.

ARSENIC ASSAY USING ELISA

TECHNICAL FIELD

This invention relates to a process for analyzing arsenic in a sample, in particular in water, comprising a detection step involving by an ELISA technique. It also relates to a kit intended to detect arsenic in a sample.

This invention finds applications in particular in the health and food safety fields.

In the description below, the references in square brackets ([ ]) refer to the list of references shown at the end of the examples.

PRIOR ART

Arsenic (As) is a chemical element widely distributed in nature. It is present in the atmosphere, soils, sediments, rocks, surface water and groundwater. Arsenic is also present in subsoil. It is the twentieth most abundant element in the earth's crust. This compound is also a major constituent of over two hundred minerals, the most common of which are arsenopyrite (FeAsS), realgar (AsS), and orpiment ($As_2S_3$).

Among metalloids and heavy metals, arsenic is one of the rare elements that can be mobilized at pH values characteristic of groundwater, that is to say between pH 6.5 and pH 8.5. The inorganic species, mainly the trivalent form arsenite (As [III]) and the pentavalent form arseniate (As[V]), are predominant. organic forms resulting from biological activity can be found occasionally, but mainly in surface water, and they are not quantitatively important. Arsenic concentration levels in water are variable, due for the most part to the geological context and the chemical characteristics of the environment considered. The highest concentration levels are found in groundwater, an environment in which the physico-chemical conditions are favourable for mobilization of arsenic. Water contamination with arsenic is generally natural, but it can also be of anthropic origin.

The contributions of arsenic in the atmosphere are due to soil erosion by wind, volcanic emissions, seawater spray, forest fires and industrial activity. The main anthropic sources are due to the melting of minerals and combustion of fossil energy sources that are rich in arsenic and produce highly toxic arsenic oxide ($As_2O_3$); copper melting and coal burning account for 60% of the emissions. The atmospheric residence time for arsenic is estimated at less than 10 days before its fallout as dust or with rain. A higher level of atmospheric arsenic is found near sites where ore is smelted and fossil energy sources rich in arsenic are burned (Bisson M., Houeix N., Hulot C., Lacroix G., Lefevre J. P., Leveque S., Magaud H., Morin A. 2006. Arsenic and its inorganic derivatives [1]).

Ingestion of arsenic, in human, can lead to acute or chronic intoxication. Acute intoxication is due to ingestion of a large amount of arsenic (1 to 2 mg/kg/d).

The acute effects of intoxication with inorganic arsenic occur within ten minutes to a few hours after ingestion. They are typically gastrointestinal, with nausea, vomiting, abdominal pain and diarrhoea. The symptoms are often accompanied by a decrease in blood pressure, convulsions, a coma linked to respiratory distress, pulmonary edema, haemolytic anaemia, and renal failure that can lead to death.

Chronic arsenic intoxication is due to ingestion of small amounts over a long period, that is to say several years. The main cause of this form of intoxication is consumption of drinking water that is contaminated with arsenic. Prolonged exposure to arsenic can lead to skin, lung, bladder and kidney cancer, together with changes in the skin such as modifications in skin pigmentation and/or hyperkeratosis. Such intoxications can also have cardiovascular effects, leading to peripheral vascular damage such as gangrene, haematological effects such as anaemia or leucopenia, damage to the nervous system and hepatic effects ([1] and World Health Organization, 2006. Arsenic mitigation for safe groundwater. EB118/14 [2]).

Moreover, inorganic arsenic (Asi) has been classified as carcinogenic for humans by the International Agency for Research on Cancer (IARC) and by the US Environmental Protection Agency (US EPA).

Thus, from 1958, the World Health Organization (WHO) took an official position on the health risks linked to the presence of arsenic in drinking water [2]. The WHO has proposed guideline values for the concentration of arsenic in drinking water. The guideline value was set at 200 µg/L, in 1958, and it has since been progressively lowered, to 50 µg/L in 1993, and then to 10 µg/L at present. Most of the industrialized countries, and in particular the USA, Europe and Japan, have transposed the value into national standards. Canada has opted for a provisional intermediate value of 25 µg/L. Many countries have maintained the 50 µg/L standard, in particular due to the technical difficulty of routine assaying of low levels of arsenic. In some developing countries, arsenic is not on the list of substances to be screened for in drinking water.

On the basis of health criteria, the guideline value for arsenic in drinking water should be less than 10 µg/L. That guideline value is conditioned by measurement limitations. It is therefore necessary for inspection organizations to have the technical possibility of screening for low concentrations of arsenic in routine.

Many countries face more or less important problems of contamination of their aquifers with arsenic. The countries with the most severe problems are Argentina, Bangladesh, Cambodia, Chile, China, the United States of America, Hungary, Mexico, Romania, Thailand and Vietnam.

The Taiyuan declaration in 2004 on water quality and arsenic mentions that twelve Asian countries are currently affected by arsenic concentrations exceeding the admissible limits. At least 50 million people are exposed to arsenic concentrations of more than 50 µg/L.

In Latin America, and especially in Argentina, Bolivia, El Salvador, Mexico, Nicaragua and Peru, 4 million people living in rural areas and consuming well water are exposed to drinking water that contains high concentration of arsenic.

Unicef, in collaboration with the government of Bangladesh, has launched a large-scale programme of drilling tube wells to provide the population with healthy water. This programme has led to drilling 8 to 12 million wells supplying almost 130 million people throughout the country. This initiative has helped to considerably reduce mortality rates among babies and children under five. Unfortunately, the country's subsoil is rich in arsenic, and water analyses showed in 1993 that many wells were fed by water contaminated with arsenic. Depending on their locations, not all the wells show the same level of contamination. Moreover, the arsenic concentration is likely to change over time.

These problems have highlighted the lack of arsenic assay methods that are easy to implement and suitable for large-scale use.

Many arsenic assay techniques have been developed. They involve use of sophisticated laboratory apparatus such as atomic absorption spectrometers or mass spectrometers, or they correspond to field kits ([2] and Hung D., Nekrassova O., Compton R. 2004. Analytical methods for inorganic arsenic in water: a review. Talanta 64:269-277 [3]).

The standards in force for assaying arsenic in drinking water recommend use of different spectroscopic methods depending on the expected concentration and the desired detection limits: hydride AAS atomic absorption spectrometry, graphite furnace atomic absorption spectrometry (GFAAS), inductively coupled plasma atomic emission spectrometry (ICP-AES) and inductively coupled plasma mass spectrometry (ICP-MS)

These methods have detection limits below the threshold value of 10 µg/L, but they entail use of apparatus that is expensive and fragile, and can only be used in a laboratory by fully trained personnel. Furthermore, none of these methods are suitable for routine analysis of large numbers of samples.

Arsenic field test kits have been developed, and they are commercially available. The detection technique used in the arsenic assay kits available is based on the appearance of a coloration that is generally assessed to the naked eye. These tests can be used in the field by non-specialized personnel, but their detection threshold is too high for water analysis, that is to say 2 mg/L.

It does not currently exist process for analyzing arsenic in samples that is both easy to use and suitable for field use, and do not require the use of sophisticated apparatus; showing a good sensitivity; enabling analysis of large numbers of samples; and being standardizable.

Moreover, the WHO states on its Web site that "Measuring arsenic content in drinking water at levels that are important for health involves laboratory analyses using complex and expensive techniques and installations, and qualified personnel that are difficult to find or finance in many regions of the world. Field analysis can be used to detect high concentrations of arsenic but they are generally not reliable at lower concentration levels that are important for human health".

In a recent report (EB118/14 dated 24 May 2006), the WHO also states that "The unavailability of a test that is simple, applicable in the field and inexpensive continues to be a significant limit to better understanding of the extent and severity of arsenic contamination of drinking-water and the development of the potential of water-quality analyses in the communities".

There is therefore a real need for a process for analyzing arsenic in samples that overcome these shortcomings, drawbacks and obstacles of the prior art, in particular a process that is easy to implement and standardizable, enabling analysis of a large number of samples, and not involving use of sophisticated, expensive apparatus, while showing a good sensitivity.

DESCRIPTION OF THE INVENTION

The invention specifically addresses these needs and overcomes the deficiencies of the prior art by providing a process and a kit for analyzing arsenic in a sample.

Thus the purpose of the present invention relates in particular to a process for analyzing arsenic in a sample, comprising the following steps:
(a) contacting a sample suspected of containing arsenic on a solid support functionalized with a DNA fragment comprising an ArsR protein binding site, site on which an ArsR protein is attached, the presence arsenic causing separation of the ArsR protein from the DNA fragment;
(b) incubation of the sample in contact with the said support;
(c) elimination of ArsR protein separated from the DNA fragment by washing the support after the incubation carried out in step (b); and
(d) analyzing by an ELISA technique to detect the presence or absence of ArsR protein remaining attached to the DNA fragment.

The process for analyzing arsenic according the present invention is based on the use of the regulating protein (ArsR) for the arsenical resistance genes of *Escherichia coli*, such as *E. coli* K12 strain MG 1655 (ATCC 47076). The ArsR protein has two binding sites: a binding site on the ars operon and an arsenic binding site.

Bacteria are frequently confronted with the presence of metals in their environment, and they have developed resistance systems (Mukhopadhyay R., Rosen B., Phung L., Silver S. 2002. Microbial arsenic: from geocycles to genes and enzymes. FEMS Microbiology Reviews 26:311-325 [4]). Arsenic can enter bacteria cells via the phosphate transport system. Most bacteria resist to this compound by expulsing it from the cell through efflux pumps. Transcription of the genes coding for the synthesis of these efflux pumps is repressed in the absence of arsenic by binding ArsR on the ars operon. The genes that compose the operon enable bacteria to resist the presence of arsenic in their environment. The binding of the ArsR protein on the operating region inhibits the expression of the bacteria's ars genes. The binding of arsenic on ArsR induces a change of conformation for the protein. This modification prevents the ArsR protein to bind to the operator or triggers release of the ArsR proteins already bound. The bacteria can thus regulate expression of their arsenical resistance genes depending on the presence or absence of arsenic in their growth environment: in the absence of arsenic, the ArsR protein binds to the operating region of the ars operon and inhibits transcription; in the presence of arsenic, the ArsR protein binds this compound and can no longer be associated with the DNA.

The inventors extracted a DNA fragment and a protein from these bacteria to develop the process of the invention. They noted that the DNA fragments and the protein conserve their activity.

The inventors are the first ones to have discovered, in a surprising way, that an analysis by ELISA technique of the presence or absence of ArsR protein bound to a DNA fragment comprising a binding site for an ArsR protein enables to analyse arsenic in a sample with an excellent sensitivity, and enables arsenic assay at much lower levels than the methods of prior art.

By "sample" it is meant any substance susceptible to contain arsenic. For example, it can consist of a liquid or a solid.

When the sample is a liquid, it can be for example water, a drink, paint, varnish, etc. For example, the drink can be milk, fruit juice, soda, flavoured water, or concentrated fruit juice. When the sample is a liquid, it can be diluted in an aqueous solution, that is to say in a solution made up mainly or solely of water.

When the sample is a solid, it can be for example food, earth, wood, ashes, etc. For example, the food can be a fruit, a vegetable, a precooked dish, meat, fish, flour, etc. When the sample is a solid, it is preferably dissolved beforehand to enable analysis of arsenic possibly present therein.

Solubilizing a solid sample may be carried out by any process known to a skilled person in the art in order to extract the arsenic possibly present in the sample and solubilize it. For example, solubilization of a solid sample can consist of a step of total or partial immersion of the sample in water and/or a saline solution and/or an acid solution enabling extraction of arsenic from the sample.

Solubilization of a solid sample can also include, for example, a step selected from the group comprising grinding, blending, agitating and a combination of these steps, in the presence of water and/or a saline solution and/or an acid solution enabling extraction of arsenic from the sample.

It is meant by "acid solution", any solution with a pH below 7. The acid solution can be, for example, any solution meeting standard ISO 11466:1995. For example, the acid solution may comprise any acid to obtain a pH below 7. For example, the acid can be selected from the group comprising hydrochloric acid, hydrofluoric acid, nitric acid, and a mixture of several of these acids. Preferably, the acid solution comprises a mixture of hydrochloric acid and nitric acid.

It is meant by "saline solution", any solution comprising a salt. For example, the salt is selected from the group comprising NaCl, $K_2HPO_4$, $KH_2PO_4$, $Na_2HPO$, $NaH_2PO_4$ and a mixture of some of these salts.

By the expression "contacting a sample suspected of containing arsenic on solid support functionalized" it is meant to the fact of arranging, depositing, placing, putting, laying or projecting a sample suspected of containing arsenic, on the surface of a solid support.

The arsenic that is to be analysed can be in any form enabling its binding to the ArsR protein. It can be, for example, in the trivalent form arsenite (As[III]) or the pentavalent form arseniate (As[V]). It can also be the antimony (Sb) which is an element equivalent to arsenic.

The expression "solid support", means any support in a solid or gel form. According to the present invention, the support can be, for example, in a nylon membrane, glass, silicon, for example porous silicon, agarose gel, polyacrylamide gel, polystyrene, polyethylene or polypropylene. The solid support can, for example, be a plate, a microplate or a tube. For example, the solid support can be a plate or a microplate comprising a plurality wells. The advantage of using a multi-well plate is to be able to perform several tests in parallel and/or provide a certain number of wells to execute control and/or pilot tests.

By the expression "solid support functionalized" it must be understood any solid support to which a molecule is attached. For example, the molecule can be a peptide, a protein or a DNA fragment, for example a DNA fragment containing a binding site for an ArsR protein.

According to the process of the present invention, the solid support can be functionalized using any means known by a skilled person in the art in order to strongly bind a molecule to the solid support, for example according to the protocol described in Sagiv J. (1980) Journal of the American Chemical Society, 102, 92 [5]. For example, the molecule can be bound by a method selected from the group comprising silanization, hydrosilylation and electrochemistry. It can consist, for example, of functionalization by streptavidin-biotin bonds. It can also consist of polystyrene or polypropylene supports that have received surface treatments to facilitate binding of organic molecules, for example those selected from among PolySorp (trademark), MediSorp (trademark), MaxiSorp (trademark), MultiSorp (trademark) and CovaLink (trademark), manufactured by Nunc.

By the expression "DNA fragment containing an ArsR protein binding site" it is meant any nucleic acid sequence on which the ArsR protein is susceptible to be bind.

The DNA fragment comprising an ArsR protein binding site can be, for example, a promoter of the arsenic resistance gene of E. coli, or a part of the promoter of the arsenic resistance gene of E. coli enabling binding of an ArsR protein. For example the promoter or the part of the promoter of the arsenic resistance gene of E. coli, is the promoter of the resistance gene to arsenic of E. coli K12 strain MG 1655, or a part of the promoter of the arsenic resistance gene of E. coli K12 strain MG 1655. For example, the sequence of the promoter of the arsenic resistance gene of E. coli can be selected from the group comprising the sequence SEQ ID NO. 1, SEQ ID NO. 17 and an active sequence having at least 80%, for example at least 85%, for example at least 90%, for example at least 95% of identity with SEQ ID NO. 1 or SEQ ID NO. 17.

The inventors have also developed DNA fragment sequences containing an ArsR protein binding site that are particularly efficient as to bind the ArsR protein in implementation of the process and the kit according to the invention. They are sequences SEQ ID NO. 23 and SEQ ID NO. 25, and their respective complementary sequences SEQ ID NO. 24 and SEQ ID NO. 26.

Thus, herein, the DNA fragment containing an ArsR protein binding site can also be, for example, a sequence selected from the group comprising SEQ ID NO. 23, SEQ ID NO. 24, SEQ ID NO. 25, SEQ ID NO. 26 and an active sequence having at least 80%, for example at least 85%, for example at least 90%, for example at least 95% of identity with SEQ ID NO. 23, SEQ ID NO. 24, SEQ ID NO. 25 or SEQ ID NO. 26. These sequences can be obtained, for example, by chemical synthesis (Eurofins MWG Operon, Edersberg, Germany).

By "active sequence", it is meant a sequence that enables binding of the ArsR protein. For example, the part of the promoter of the arsenic resistance gene of E. coli can have a size of less than 100 base pairs.

The ArsR protein has a binding site to a DNA fragment containing an ArsR protein binding site and an arsenic binding site. In the absence of arsenic, and when a DNA fragment containing an ArsR protein binding site is present, the ArsR protein binds to the ArsR protein binding site of the DNA fragment. It is meant by "binding of the ArsR protein to the DNA fragment", non-covalent interactions, such as hydrogen bonds, which are established between the ArsR protein and the DNA fragment in the absence of arsenic. In the presence of arsenic, the latter binds to the arsenic binding site of the ArsR protein via arsenic-thiol bonds between the arsenic molecule and the sulphur atoms of the cysteines of the ArsR protein. The binding of arsenic on the arsenic binding site of the ArsR protein induces a change of conformation of the ArsR protein that triggers separation of the ArsR protein from the DNA fragment.

According to the present invention, the ArsR protein can be a natural or modified ArsR protein.

It is meant by "natural ArsR protein", an ArsR protein obtained from the gene encoding this protein without the sequence of the gene or the ArsR protein has been modified. For example, the ArsR protein can be obtained from E. coli K12 strain MG 1655 using purification techniques that are well known to a skilled person (J C Janson, L Ryden (1998). Protein purification: Principles, High-Resolution Methods, and Applications. Second edition, Wiley-VCH ISBN-10: 0-471-18626-0 [6]). The ArsR protein obtained from E. coli K12 strain MG 1655 has sequence SEQ ID NO. 4.

It is meant by "modified ArsR protein", an ArsR protein obtained from the gene encoding this protein and whose sequence has been modified, or by post-translational modification of the ArsR protein. For example, the ArsR protein can be modified by genetic recombination, for example according to the protocol described in F. Cordier-Ochsenbein et al. (Cordier-Ochsenbein, F., R. Guerois, et al. (1998). "Exploring the folding pathways of annexin I, a multidomain protein. II. Hierarchy in domain folding propensities may govern the folding process." J Mol Biol 279(5): 1177-85 [7]).

The ArsR protein can for example be modified in such a way that the last 20 amino acids making up its sequence are removed (Xu and Rosen (1997) Dimerization is essential for DNA binding and repression by the ArsR metalloregulatory protein of *Escherichia coli*. J. Biol. Chem., Vol. 272, No. 25, pp. 15734-15738 [8]). The use of this type of truncated ArsR protein facilitates expression of the ArsR protein in a soluble form.

As a complement or an alternative to the aforementioned modifications, the ArsR protein can be modified, for example, so that it is covalently bonded to a recognition peptide ("tag") of known sequence, for implementation of the ELISA test.

The recognition peptide can be, for example, synthesized chemically, for example by chemical synthesis on a solid support, for example according to a process described in "Fmoc Solid Phase Peptide Synthesis: A Practical Approach (Practical Approach Series) W. C. Chan (Editor), Peter D. White (Editor)", Oxford Univ Press 2000" [9].

The recognition peptide can be bonded to the ArsR protein by any means known to a skilled person in the art. For example, a recognition peptide can be bonded to the ArsR protein by synthesis of a sequence of amino acids corresponding to the succession of the sequence of the recognition peptide and the sequence of the ArsR protein.

Preferably, the recognition peptide is bonded covalently to the ArsR protein, for example by a peptide bond.

According to the present invention, the sequence of the recognition peptide can be selected from among SEQ ID NO. 10, SEQ ID NO. 11, SEQ ID NO. 12, SEQ ID NO. 13, SEQ ID NO. 14, SEQ ID NO. 15, SEQ ID NO. 16 and a sequence enabling such marking having at least 80%, for example 85%, for example 90%, for example 95% of identity with these sequences.

The inventors have developed modified ArsR proteins that are particularly efficient for implementation of the process and the kit according to the invention. They are modified ArsR proteins of sequences SEQ ID NO. 9 and SEQ ID NO. 22.

According to the invention, the ArsR protein, whether natural or modified, can be an ArsR protein of sequence selected from the group comprising SEQ ID NO. 4, SEQ ID NO. 9, SEQ ID NO. 22 and a sequence enabling such marking and having at least 80%, for example 85%, for example 90%, for example 95% of identity with these sequences.

According to the process of the present invention, the contacting step (a) can be carried out in any conditions enabling an interaction between the arsenic susceptible to be contained in the sample and the solid support. It can for example be carried out at any pH level enabling an interaction between arsenic and the ArsR protein. For example, whatever the nature of the sample, that is to say whether the sample is a liquid or solid sample, solubilized in water and/or a solvent or not, that sample can be mixed with a buffer solution to stabilize the pH level of the sample. Contacting step (a) can, for example, be carried out with a buffer solution that has a pH level lying between 6 and 8. Preferably, contacting step (a) is carried out with a solution that has a pH level of 7.4. For example, the buffer solution is selected from the group comprising the phosphate buffer saline (PBS) and the Tris buffer saline (TBS).

According to the invention, incubation step (b) can be carried out for any length of time and at any temperature enabling an interaction between the arsenic and the ArsR protein.

It is meant by "incubation", the fact of leaving the sample in contact with the solid support. Incubation step (b) can be carried out under any conditions enabling an interaction between the arsenic susceptible to be contained in the sample and the solid support. It can for example be carried out at any temperature and for any length of time enabling interaction between arsenic and the ArsR protein.

According to the invention, incubation step (b) can be carried out for a period ranging from 1 minute to 90 minutes, for example from 30 to 90 minutes, for example from 40 to 80 minutes, for example from 50 to 70 minutes, for example for 60 minutes.

According to the invention, incubation step (b) can be carried out at a temperature ranging between 15 and 37° C., for example between 20 and 30° C., for example at 25° C.

According to the invention, step (c) of elimination of any ArsR protein possibly separated from the DNA fragment can be carried out by any means known to a skilled person in the art, enabling elimination of the ArsR proteins separated from the DNA fragment, without releasing the ArsR proteins bound to the DNA fragment. It can be for example the use of a washing solution. The washing solution can be for example selected from the group comprising water, for example distilled water and a buffer solution. For example the buffer solution is selected from the group comprising a PBS, a TBS, a PBS containing 0.05% of Tween (PBST), and a TBS containing 0.05% of Tween (TBST). The skilled person in the art is able to determine the quantity of washing solution and the number of washing sequences required.

It is meant by "arsenic analyzing process", any process enabling the determination of the presence or absence of arsenic and/or the quantity of arsenic present in the sample.

According to the process of the present invention, step (d) of analysis by an ELISA technique can comprise a step of observing the presence or absence of ArsR protein remaining bound to a DNA fragment comprising an ArsR protein binding site. The arsenic analysis process according to the present invention can also comprise a step of measuring the quantity of ArsR protein remaining bound to that DNA fragment.

It is meant by "observing", the fact of looking, for example in the naked eye or under a microscope, for example for the absence of coloration or luminescence, or the coloration or luminescence for example produced by a reaction of a substrate with an enzyme, the substrate and the enzyme being defined below. The absence of coloration translates the presence of arsenic, whereas coloration translates the absence of arsenic in the analysed sample. The observation can be for example compared with a control solution containing arsenic at a determined concentration or with several control solutions containing arsenic at different determined concentration.

Observing can also include a step of measurement of the coloration or luminescence. For example the coloration can be measured using a spectrophotometer. For example, the luminescence can be measured using a luminometer.

According to the present invention, it is meant by "ELISA (Enzyme Linked ImmunoSorbent Assay) technique", any immuno-enzyme detection technique enabling visualizing of an antigen-antibody reaction with a coloured reaction produced by the action of an enzyme previously bound to the antibody on a substrate. Preferably, the ELISA technique is a direct or indirect ELISA technique.

By "direct ELISA technique", it is meant a technique involving antibodies conjugated with an enzyme directed against the ArsR protein or towards a recognition peptide bound to the ArsR protein.

By "indirect ELISA technique" it is meant a technique involving two categories of antibodies. The first category of antibodies is directed against the ArsR protein or towards a recognition peptide bound to the ArsR protein, and the second category of antibodies is coupled with an enzyme and directed against the first category of antibodies.

The principle of the ELISA techniques can for example be consulted in ELISA, Methods in Molecular Biology, 1995, Volume 42, Part 1, 35-61, DOI: 10.1385/0-89603-279-5:35 [10].

The skilled person in the art is able to determine which antibodies, enzymes and substrate can be used.

Whatever the ELISA technique used, the antibody directed against the ArsR protein can be obtained by a process described in "Protocols for preparing immunogens, immunization of animals, and collection of antiserum may be found in *Antibodies: A Laboratory Manual*, E. Harlow and D. Lane, ed., Cold Spring Harbor Laboratory (Cold Spring Harbor, N.Y., 1988) pp. 55-120" [11].

Examples of antibodies conjugated with an enzyme and directed against a recognition peptide bound to the ArsR protein are shown in table 1 below, associated with the sequences of the corresponding recognition peptides.

TABLE 1

Recognition peptides and antibodies conjugate with an associated enzyme

| Sequence of the recognition peptides | SEQ ID NO. | Antibody directed against the sequence | Conjugate enzyme | Product reference and Suppliers |
|---|---|---|---|---|
| DYKDDDDKG (Flag) | 10 | Anti-flag antibody | Alkaline phosphatase | A469 Sigma Aldrich |
| GKPIPNPLLGLDST (peptide v5) | 11 | Anti-V5 antibody | Horseradish peroxydase (HRP) | V2260 Sigma Aldrich |
| HHHHHH (His) | 12 | Anti-polyhistidine antibody | Alkaline phosphatase | A5588 Sigma Aldrich |
| EQKLISEEDL (c-MYC) | 13 | Anti-c-Myc antibody | Alkaline phosphatase | A5963 Sigma Aldrich |
| YPYDVPDYA (HA) | 14 | Anti-HA antibody | Alkaline phosphatase | A5477 Sigma Aldrich |
| YTDIEMNRLGK (VSV-G) | 15 | Anti-VSV-G antibody | Horseradish peroxydase (HRP) | A5977 Sigma Aldrich |
| TDFYLK (AU5) | 16 | Anti-AU5 antibody | Horseradish peroxydase (HRP) | NB600-462 Novus Biologicals Inc. |

Examples of enzymes bound to the antibodies and corresponding substrates that can be used are shown in table 2 below. There are various types of substrates, namely chromogenic, chemiluminescent, and fluorescent substrates.

TABLE 2

Enzymes and associated substrates

| Enzyme | Substrate | Product reference and Suppliers |
|---|---|---|
| Alkaline phosphatase | Alkaline Phosphatase Blue Microwell Substrate | AB0100 Sigma Aldrich |
| Alkaline phosphatase | Alkaline Phosphatase Red Microwell Substrate | AB0200 Sigma Aldrich |
| Alkaline phosphatase | 4-Nitrophenyl phosphate disodium salt hexahydrate (pNPP) | P4744-1G Sigma Aldrich |
| Alkaline phosphatase | Disodium 2-chloro-5-(4-methoxyspiro{1,2-dioxetane-3,2'-(5'-chloro)tricyclo[3.3.1.13,7]decan}-4-yl) phenyl phosphate (CDP-Star) | 12 041 677 001 Roche Diagnostics |
| Horseradish peroxydase (HRP) | 3,3',5,5'-tetramethylbenzidine (TMB) | T4444 Sigma Aldrich |
| Horseradish peroxydase (HRP) | Diammonium 2,2'-azino-bis(3-ethylbenzothiazoline-6-sulfonate | A9941 Sigma Aldrich |
| Horseradish peroxydase (HRP) | 5-Amino-2-hydroxybenzoic acid | A6178 Sigma Aldrich |
| Horseradish peroxydase (HRP) | Chemiluminescent Peroxidase Substrate | CPS260 Sigma Aldrich |
| Horseradish peroxydase (HRP) | 4-Methylumbelliferyl-phosphoric acid | M8883 Sigma Aldrich |

According the invention, the highest sensitivity is obtained with fluorescent substrates, followed by chemiluminescent substrates, and lastly chromogenic substrates. Preferably, the substrates used in test laboratories are chemiluminescent or fluorescent substrates, because showing an higher sensitivity. Preferably, the substrates used in the field are chromogenic substrates, because showing an enhanced stability.

According to the process of the present invention, step (d) of analysis by an ELISA technique can, for example, include the following steps:
(i) adding an antibody directed against the ArsR protein, said antibody being conjugated to an enzyme, for example the antibody and the enzyme being those defined above,
(ii) incubation of the antibody in contact with the ArsR protein,
(iii) elimination of the antibodies that are not bound to the ArsR protein by washing the support after the incubation carried out at step (ii),
(iv) adding a substrate producing coloration after reacting with the enzyme, for example a substrate defined above.

According to the invention, step (ii) of incubation can be carried out for any length of time and at any temperature enabling an interaction between the ArsR protein and the antibody directed against the ArsR protein. It can be carried out for example for a period ranging from 1 minute to 90 minutes, for example from 30 to 90, for example from 40 to 80 minutes, for example from 50 to 70 minutes, for example for 60 minutes. It can be carried out for example at a temperature ranging between 15 and 37° C., for example between 20 and 30° C., for example at 25° C.

According to the invention, step (i) of contacting can be carried at any pH enabling an interaction between the ArsR protein and the antibody directed against the ArsR protein. For example, step (i) of contacting can be carried out with a buffer solution that has a pH comprised between 6 and 8. Preferably, step (i) of bringing into contact is carried out with a solution that has a pH level of 7.4. For example, the buffer solution can be phosphate buffer saline containing 0.05% of Tween and containing 1% (weight/volume) of protein solution (PBSTBr). The proteins can for example be selected from among the group comprising a blocking reagent N° 11 096 176 001 (skimmed milk proteins) (Roche Diagnostics GmbH), a blocking reagent N° 11 112 589 001 (proteolytic digestion of purified gelatin) (Roche Diagnostics GmbH) and bovine serum albumin (BSA).

According to the invention, step (iii) of elimination of the antibodies that are not bound to the ArsR protein can be carried out with any washing solution known to a skilled person in the art, enabling elimination of the ArsR proteins separated from the DNA fragment, without releasing the ArsR proteins bound to the DNA fragment. It can be for example of a washing solution selected from the group comprising a PBS, a TBS, a PBS containing 0.05% of Tween (PBST), and a TBS containing 0.05% of Tween (TBST). Step (iii) of elimination of the antibodies that are not bound to the ArsR protein can be carried out for example by application of a washing solution on the solid support. A washing control can be achieved by searching in the buffer solution stemming from the washing the presence of the ArsR protein, for example using antibodies directed against the ArsR protein or a recognition peptide, said antibodies being defined above.

According to the present invention, the process can also comprise a step (e) of comparison of the measurement carried out at step (d) with a control sample containing arsenic. This step enables comparison of a sample with a solution containing a known arsenic concentration, thus enabling users to determine whether the arsenic concentration in the sample is greater than, lower than or equal to the control sample containing arsenic. For example the control sample comprising arsenic can consist of several solutions containing arsenic at different concentrations, thus providing a standard range.

The process according to the present invention can also comprise a step (f) of comparison of the measurement carried out at step (d) with a control sample containing no arsenic. This step ensures that the analysis does not contain contamination.

According to a particular embodiment of the invention, the ArsR protein can be bound subsequently to the functionalization of the solid support with a DNA fragment containing an ArsR protein binding site. For example, the ArsR protein can be added before contacting the sample susceptible of containing arsenic with the solid support. The ArsR protein can also be added to the sample before contacting the sample with the solid support.

The invention also relates to a kit for detection of arsenic in a sample, said kit comprising:
a solid support functionalizable or functionalized with a DNA fragment comprising an ArsR protein binding site,
a DNA fragment containing an ArsR protein binding site;
an ArsR protein;
a means for detection by ELISA of the presence of the ArsR protein.

Examples of solid supports, DNA fragments, and ArsR protein are defined above. For example, the solid support can be a plate or a microplate comprising a plurality of wells.

According to the invention, the means for detection by ELISA of the presence of the ArsR protein can, for example, be a detection means using colorimetry or luminescence. It can be, for example, the antibodies, enzymes and substrates defined above.

According to the invention, the kit can also comprise arsenic at a determined concentration. For example, the kit comprises several solutions containing arsenic at different concentrations, enabling determination of a standard range.

The present invention provides therefore a process for analyzing arsenic in a sample that is easy to implement and standardizable, enabling analysis of a large number of samples, and not requiring the use of sophisticated and expensive apparatus, while showing good sensitivity. The present invention also provides a kit for assaying arsenic in a sample, enabling implementation of the process according to the invention on the field.

Other advantages may yet be found by a skilled person in the art upon reading the following examples, illustrated by the attached figures, which are provided for information purposes only and not being limitative.

"Biot" means biotin, "As/ArsR" means arsenic bound to the ArsR protein and "L" means light emission during transformation of the substrate by the alkaline phosphatase.

Figure 2:
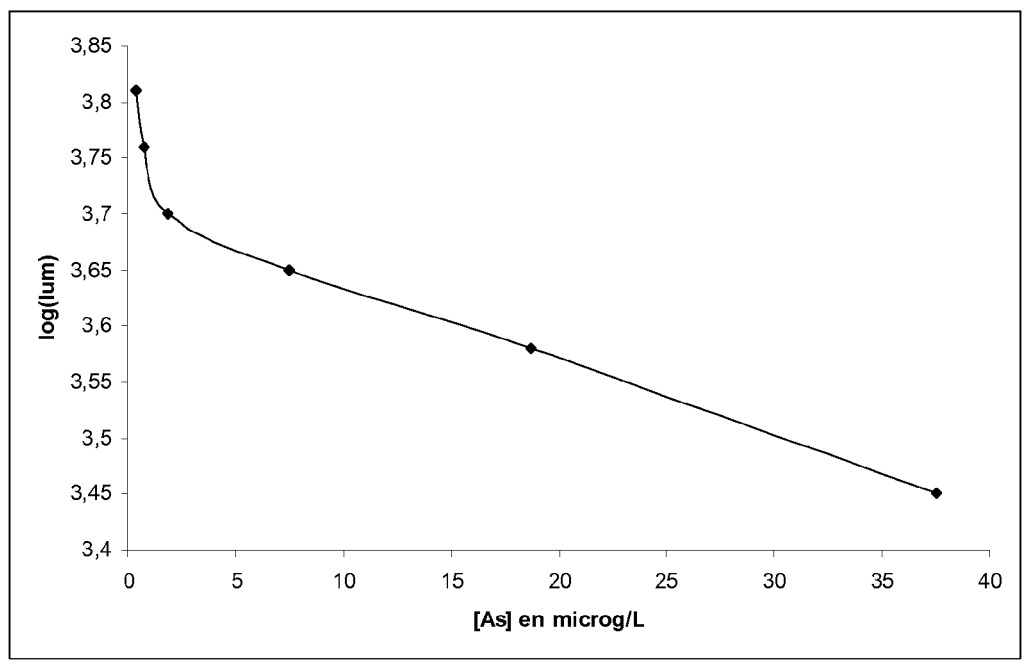

FIG. 2 represents a model curve of the variations in luminescence depending on the arsenic concentration (0.375 µg/L, 0.750 µg/L, 1.875 µg/L, 7.500 µg/L, 18.750 µg/L and 37.500 µg/L). The x-axis represents the arsenic concentration ("[As]") expressed in micrograms per liter (microg/L or µg/L). The y-axis represents the logarithm of the luminescence value ("log(lum)").

Figure 3:
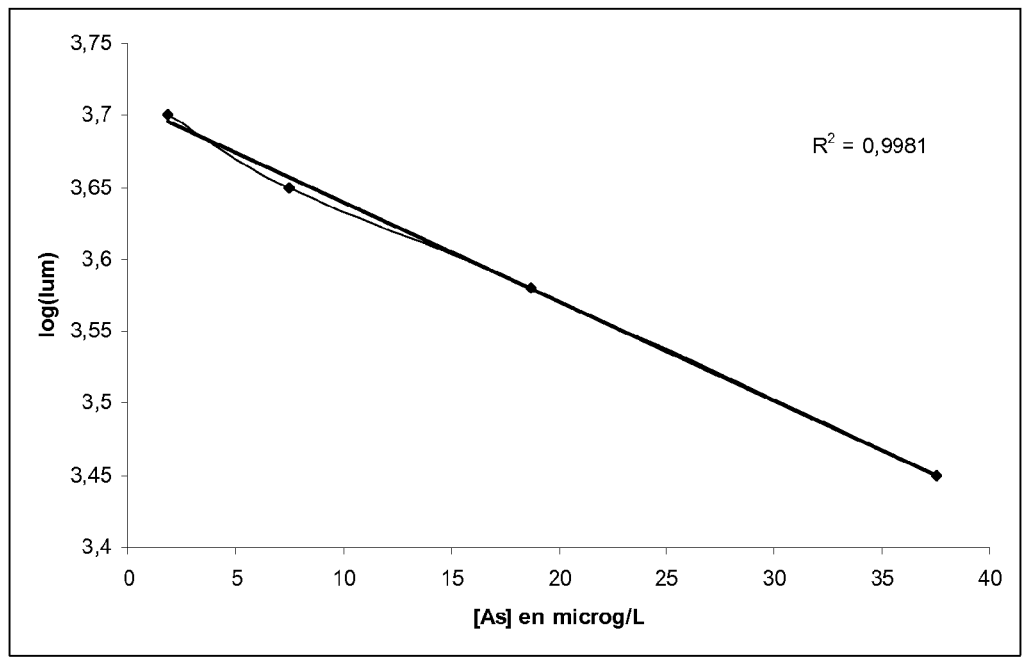

FIG. 3 represents a standard curve of the variations in luminescence depending on the arsenic concentration executed on the basis of dilution of arsenic at known concentrations (1.875 µg/L, 7.500 µg/L, 18.750 µg/L and 37.500 µg/L). The x-axis represents the arsenic concentration ("[As]") expressed in micrograms per liter (microg/L or µg/L). The y-axis represents the logarithm of the luminescence value ("log(lum)"). "$R^2$" represents the multiple determination coefficient.

Figure 4:
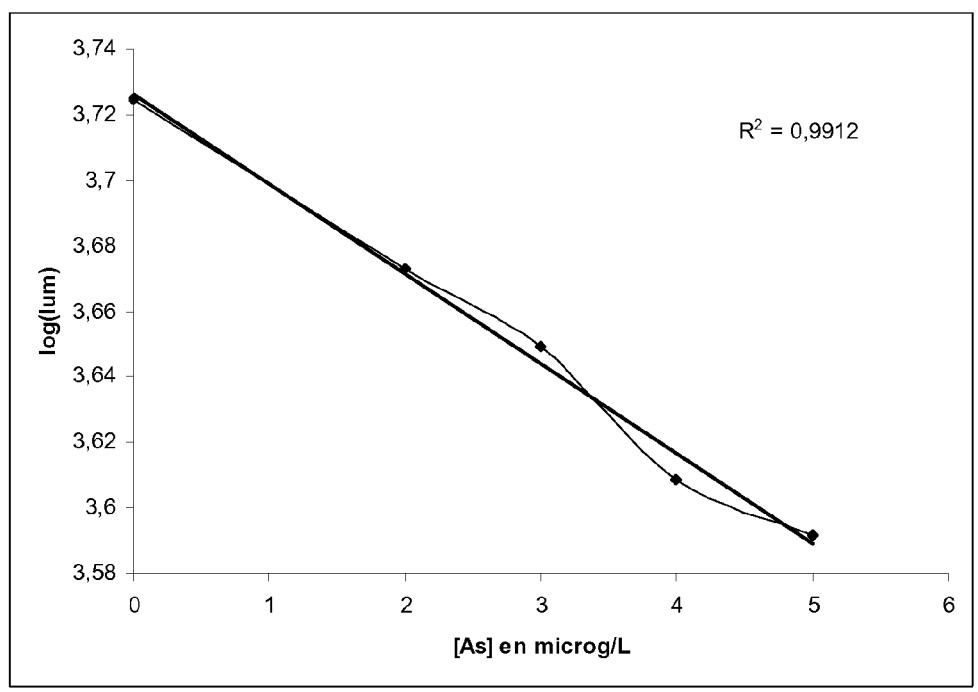

FIG. 4 represents a standard curve of the variations in luminescence depending on the arsenic concentration executed on the basis of dilution of arsenic at known concentrations (0 µg/L, 2 µg/L, 3 µg/L, 4 µg/L, 5 µg/L). The x-axis represents the arsenic concentration ("[As]") expressed in micrograms per liter (microg/L or µg/L). The y-axis represents the logarithm of the luminescence value ("log(lum)"). "$R^2$" represents the multiple determination coefficient.

EXAMPLES

In the examples below, the following compositions have been used:
PBS: Phosphate, 10 mM; NaCl, 137 mM; KCl, 2 mM; pH 7.4±0.1.
PBST: PBS containing 0.05% (volume/volume) of Tween 20.
PBSTBr: PBST containing 1% (weight/volume) of solution of blocking reagent N° 11 096 176 001 (Roche Diagnostics GmbH) used to limit the non-specific binding of the antibodies on the support.
PBSTLE: PBST containing 5% (weight/volume) of skimmed milk used to limit non-specific binding of the proteins and the antibodies on the support.
CDP*: Chemiluminescent substrate of alkaline phosphatase.
Buffer 1: TrisHCl, 100 mM; NaCl, 100 mM; $MgCl_2$, 50 mM; pH 9.5±0.1.

Example 1

Principle of an Analyzing Process in Conformity with the Invention

Figure 1:
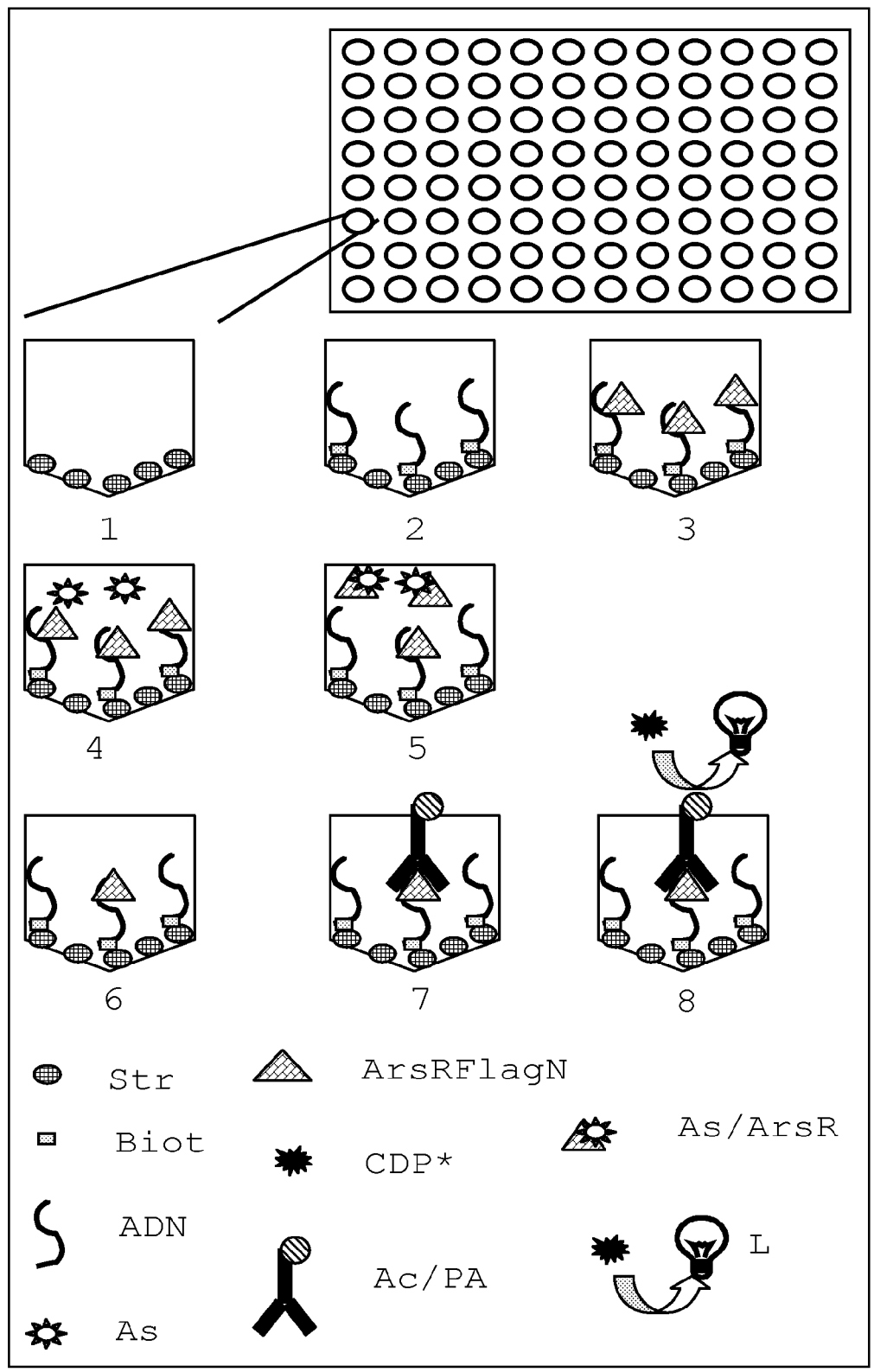
FIG. 1 shows the principle of the immuno-enzymatic arsenic assay method according to the present invention. A microplate with 96 wells is shown in the upper right-hand corner. Below, are shown in an enlarged manner, the wells of the microplate, wherein: the well (1) is functionalized with streptavidin ("Str"), the well wherein (2) a biotinyl DNA fragment containing an ArsR protein binding site is added, the well wherein (3) ArsR proteins to which a Flag peptide is bound in N-terminal position ("ArsRFlagN") are added and binds to the ArsR protein binding sites of the DNA fragment, the well wherein (4) arsenic ("As") is added, the well wherein (5) the arsenic binds to ArsRFlagN proteins that separate out from the DNA fragment, the well wherein (6) the separated ArsRFlagN proteins and the arsenic are eliminated, the well wherein (7) anti-Flag antibodies coupled with alkaline phosphatase ("Ac/PA") are added and bind to the remaining ArsR-FlagN proteins, and the well wherein (8) a substrate of alkaline phosphatase ("CDP*") is added, resulting in light emission.

This Principle Is Illustrated By FIG. 1. The Figures In Brackets correspond to the figures shown in FIG. 1.

Details of each of these steps are shown in examples 2, 3 and 4 below.

Streptavidin is bound to the bottoms of the wells in the microplate (1).

The DNA fragment is added in the wells of the microplate (2). The unbound DNA fragments are eliminated by washing.

The raw protein extract containing the ArsR protein is added in the wells (3) to enable the protein to bind to its site on the DNA. The unbound proteins are eliminated by washing.

Different dilutions of arsenic solution to be assayed are added (4), the arsenic binds to the ArsR protein (5) that is separated from its site. These proteins are eliminated by washing. Only the ArsR proteins that have not bound arsenic remain attached to the DNA (6).

A specific antibody of the Flag sequence is added (7). That antibody binds the Flag sequence of the ArsR protein bound to the DNA. The antibody is coupled with an enzyme, alkaline phosphatase for example. Any antibodies not bound are eliminated by washing.

A substrate of the enzyme is added in the wells. Light is emitted when the substrate is cleaved by the enzyme (8). The quantity of light emitted is proportional to the quantity of enzyme present and hence to the quantity of ArsR protein bound to the DNA, which depends on the arsenic content. The quantity of arsenic contained in the sample is obtained by comparing the results with a standard curve.

Example 2

Microplate Functionalization with a DNA Fragment Containing an ArsR Protein Binding Site In this example, the used DNA fragment containing the binding site of the ArsR protein is composed of 254 base pairs (SEQ ID NO. 1, called "Opars1" herein). Opars1 sequence has been obtained by PCR (DNA polymerase chain reaction) amplification using the primers Opars1L (SEQ ID NO. 2) and Opars1R (SEQ ID NO. 3). The chromosomal DNA of the *Escherichia coli* K12 bacteria strain MG1655 (ATCC 47076) was used as a template for the PCR amplification. Biotin was added on the nucleotide at position 5' during synthesis of the Opars1L primer. Biotinylated Opars1 sequences, that is to say sequences with a biotin in position 5', were thus obtained.

A "NUNC Immobilizer (trademark) Streptavidin" microplate (Nunc Streptavidin Microplate, Dominique Dutscher (ref. 056212), Brumath, France) with 96 wells with a useful volume of 100 µl each and whose surface is functionalized with streptavidin, was used. The wells of this microplate were washed three times using 300 µl of PBST solution.

A solution containing Opars1 DNA fragments was diluted in PBS solution to obtain a DNA concentration of 0.2 µM. 100 µl of that solution were placed in each well of the "NUNC Immobilizer (trademark) Streptavidin" microplate. The microplate was incubated for 60 minutes at 25° C., to enable binding of the DNA in the wells.

Biotin and streptavidin have a very high affinity and are able to bind spontaneously. The presence of a biotin on the Opars1 sequence thus enabled binding of the Opars1 sequence to the surface of the wells functionalized with streptavidin.

The unbound DNA was eliminated by three successive washes using 300 µl of PBST per well.

Example 3

Binding of an ArsR Protein on the Opars1 Sequence Functionalized on a Microplate The ArsR protein of sequence SEQ ID NO. 4 corresponds to the protein that regulates the Ars operon of *Escherichia coli* K12 strain MG1655. The arsR gene of sequence SEQ ID NO. 5 coding that protein was amplified from the chromosomal DNA of that strain using the primers arsRR (SEQ ID NO. 6) and arsRL (SEQ ID NO. 7), and cloned in expression vector pQE70 (Qiagen) according to the protocol described in the document "The QiaExpressionist: A handbook for high-level expression and purification of 6×His-tagged proteins. June 2003. Fifth ed., Qiagen" [12]. A Flag sequence (SEQ ID NO. 10) was inserted in the N-terminal region of the ArsR protein and named "ArsRFlagN" (SEQ ID NO. 9). The Flag sequence is recognized by anti-Flag antibodies (Ref. A9469, Sigma Aldrich, Saint-Quentin Fallavier, France). This addition will allow detecting and assaying the ArsR protein more efficiently.

The plasmid pQE70 containing the arsRFlagN gene (SEQ ID NO. 8) coding for the ArsRFlagN protein was named "pQEarsRFlagN" and was introduced in the *Escherichia coli* strain M15[pREP4] (Qiagen SA, Courtaboeuf, France) to produce the ArsRFlagN protein.

50 ml of LB medium containing 100 mg/L of ampicillin were inoculated with a preculture of the M15[pREP4]/pQEarsRFlagN strain and placed under agitation at 37° C.

When the optical density of the culture reached a value of 0.5, the production of the protein was induced by adding 0.4 mM of IPTG (isopropyl β-D-1-thiogalactopyranoside) for 15 minutes. This protein production period was selected to limit precipitation of the ArsRFlagN protein in inclusion bodies. The cells were then recovered by centrifugation at 4,000×g for 15 minutes at 4° C. The cells were then washed in PBS buffer. The bacterial pellet was resuspended in 1 ml of PBS buffer. Then the cells were lysed using a vibratory ball mixer mill (MM301 mixer mill, Retsch) ("bead beater"), which is a mechanical system for cell lysis by agitation in the presence of glass beads of 0.1 mm in diameter. The protein extract was centrifuged for 30 minutes at 30,000×g at 4° C. to eliminate the cell debris. The supernatant was recovered and cold-stored in ice for immediate use or deep frozen (−80° C.).

The amount of soluble ArsRFlagN protein thus produced was estimated at 200 μg.

The 200 μg of ArsRFlagN proteins produced were diluted to 1/100 in PBST buffer. 100 μl of that solution were added in each of the assay wells. The microplate was incubated for 60 minutes at 25° C., to enable the attachment of the ArsRFlagN proteins on the DNA in the wells. The amount of ArsRFlagN proteins added per well was estimated at about 0.4 μg.

The unbound proteins were eliminated by three successive washes using 300 μl of PBST per well.

Example 4

Enzyme-Linked Immunosorbent Assay (ELISA) Method for Arsenic

A DNA fragment containing the ArsR protein binding site was attached to a support in the same way as that set out in example 2 above.

A solution containing the ArsR protein was added according to the protocol presented in example 3 above, to enable the protein to bind with the DNA.

6 dilutions of arsenic solution, at 0.375 μg/L, 0.750 μg/L, 1.875 μg/L, 7.500 μg/L, 18.750 μg/L and 37.500 μg/L respectively, were prepared in PBS to provide a standard range. 100 μl of each of these dilutions were added respectively in a microplate well.

The microplate was incubated for 60 minutes at 25° C., to enable the arsenic to bind with the ArsRFlagN proteins.

The unbound ArsRFlagN proteins were eliminated by three successive washes using 300 μl of PBST per well.

100 μl of a solution of anti-Flag antibody (Ref. A9469, Sigma Aldrich, Saint-Quentin Fallavier, France), conjugated with alkaline phosphatase, were added in each wells. The antibody was previously diluted in PBSTBr in compliance with the supplier's recommendations. The microplate was incubated for 60 minutes at 25° C. to enable the antibody to bind with the ArsRFlagN proteins.

The unbound anti-Flag antibodies were eliminated by three successive washes using 300 μl of PBST per well.

A CDP* solution at 0.25 mM was prepared in buffer 1. 100 μl of CDP* solution were placed in the different assay wells. The light emitted was immediately measured using a luminometer (LumiStar, BMG Lab Technologies).

The principle of the method presented in examples 1 to 4 is illustrated by FIG. 1.

The luminescence values (L) obtained are shown in table 3 below and illustrated by FIGS. 2 and 3.

TABLE 3

Measurement of luminescence depending on arsenic concentration

| Concentration of AsIII (μM) | Concentration of AsIII (μg/L) | Luminescence value (L) | logL |
|---|---|---|---|
| 0.005 | 0.375 | 6,426 | 3.81 |
| 0.01 | 0.750 | 5,808 | 3.76 |
| 0.025 | 1.875 | 5,023 | 3.70 |
| 0.100 | 7.500 | 4,422 | 3.65 |
| 0.250 | 18.750 | 3,776 | 3.58 |
| 0.500 | 37.500 | 2,831 | 3.45 |

The standard curve obtained is linear (FIG. 3) as from 1.875 μg/L of arsenic, showing that the sensitivity of the technique is well below the detection limit of 10 μg/L for current methods.

Furthermore, the coefficient of determination $R^2=0.9981$, which is an indicator for judging the quality of a linear regression, in particular when measuring adequacy between the model (FIG. 2) and the data observed (FIG. 3), confirms the reliability of the results observed.

Such results had never been obtained. The process according to the present invention could hence well become the reference process for assaying arsenic in a sample.

Example 5

Expression and Purification of an ArsRFlagN-6His Protein

The sequence of the wild type arsR gene of *Escherichia coli* was modified using methods described by Sorensen et al. or Zhang et al. (Sorensen M A, Kurland C G, Pedersen S. (1989), Codon usage determines translation rate in *Escherichia coli*. J Mol. Biol. 1989; 207(2):365-77 [13]; Zhang S P, Zubay G, Goldman E., Low-usage codons in *Escherichia coli*, yeast, fruit fly and primates. Gene. 1991; 105(1):61-72 [14]) to enable enhanced expression of the ArsR protein. The gene of sequence SEQ ID NO. 18 was thus synthesized. This DNA fragment contains an NcoI restriction site: CCATGG, the Flag sequence: GACTACAAAGACGACGACGACAAA (SEQ ID NO. 19), the optimized sequence of the arsR gene: GGTAGCTTTCTGCTGCCGATCCAGCTGT-TCAAAATTCTGGCAGACGAA ACCCGTCTGGGTAT-TGTGTTACTGCTGAGCGAATTAGGCGAACTGTGC GTTTGCGATCTGTGTACCGCGTTAGAT-CAGAGTCAGCCGAAAATTAGC CGTCATCTGGCGT-TATTACGCGAAAGCGGTCTGTTACTGGACCGTAAA CAGGGCAAATGGGTCCATTACCGCT- TATCTCCGCATATTCCGGCTTGG GCAGCAAAAAT-CATTGACGAAGCCTGGCGTTGCGAACAGGAAAAA GTT CAGGCGATCGTCCGTAACCTGGCACGTCAAAA TTGTAGCGGCGATAG CAAAAACATC (SEQ ID NO. 20) and an XhoI site: CTCGAG. The NcoI and XhoI restriction sites were introduced respectively at the beginning of the sequence (region 5' of the gene) and at the end of the sequence (region 3'). These restriction sites enable cloning of the arsR gene in the expression vector pET28b(+) commercialized by the Novagen Company (Cat. No. 70777, Merck, Lyons, France). The vectors of the pET series were developed to facilitate expression and purification of recombinant proteins in Escherichia coli (Rosenberg, A. H., Lade, B. N., Chui, D., Lin, S., Dunn, J. J., and Studier, F. W. (1987) Vectors for selective expression of cloned DNAs by T7 RNA polymerase. Gene 56 (1): 125-135 [15]). The gene of sequence SEQ ID NO. 18 was cloned in vector pET28b(+), under the dependence of a strong promoter of bacteriophage T7 according to the protocol described in the technical instructions supplied with the vector (pET System Manual, Novagen, TB055 8th Edition February 99). Gene transcription was carried out by polymerase T7 synthesized by E. coli (host strain for expression of the recombinant protein). The polymerase was synthesized the Escherichia coli expression strain only in the presence of an inducer: isopropyl β-D-1-thiogalactopyranoside (IPTG). It was therefore possible to finely regulate the level of expression of the protein and obtain high yield. The pET28b(+) vector carries a kanamycin resistance gene (selection and maintaining of the plasmid) and two polyhistidine sequences in the multiple cloning site. These sequences enabled introduction of a polyhistidine tail: HHHHHH (SEQ ID NO. 12) from arsRFlagN after cloning in the pET-28b(+) vector, in the N- or C-terminal region of the recombinant protein, which facilitates purification. This polyhistidine sequence can bind on a resin containing nickel or cobalt. The recombinant protein was thus retained, whereas the other proteins were eluted. The sequences of the gene cloned in the pET28b(+) vector and the corresponding to arsRFlagN-6His protein are presented respectively in sequences SEQ ID NO 21 and SEQ ID NO 22.

The construction was introduced, by transformation, in the bacteria Escherichia coli C43(DE3) pLysS (Miroux and Walker, Over-production of proteins in Escherichia coli: mutant hosts that allow synthesis of some membrane proteins and globular proteins at high levels. J Mol. Biol. 1996; 260 (3):289-98 [16]) (F-ompT hsdSB (rB- mB-) gal dcm (DE3) pLysS CmR) commercialized by the Lucigen Company (Euromedex, Souffelweyersheim, France).

A overnight culture in LB-Glucose medium (composition per liter of medium: 10 g of tryptone, 5 g of autocatalytic yeast extracts, 5 g of NaCl, 10 g of glucose) supplemented with 25 mg of kanamycin per liter of medium was used to inoculate a liter of identical medium. The bacteria were grown under agitation, at 37° C., up to an optical density of 0.5 at 600 nm. Protein production was then induced by adding 0.5 mM of IPTG. The cells induced were maintained under agitation, at 37° C., for 3 hours. The cells were then recovered by centrifugation (9,000×g, 10 minutes, 4° C.). The pellet was resuspended in PBS buffer, and then cells were recovered by centrifugation, as set out above. The cells were resuspended in PBS buffer supplemented with 10 mM of imidazole (4 ml of buffer per gram of bacterial pellet). A cocktail of protease inhibitors (Protease Inhibitor cocktail Set III without EDTA, Cat. No. 539 134, Calbiochem, Merck, Lyons, France) was added (1 ml per 40 ml of bacterial suspension). The cells were lysed using a mechanical method (two passages at 1,500 bar through a cell disintegrator, OneShot model, Constant Systems Ltd., CellD, Sauveterre, France). The lysate was centrifuged at 35,000×g at 4° C. for 30 minutes. The supernatant was recovered and then clarified by passage through a 0.22 µm filter.

The ArsRFlagN-6His protein (SEQ ID NO. 22) was purified by affinity chromatography (IMAC). An Ni-NTA column was balanced with PBS buffer+10 mM of imidazole. The clear lysate was deposited on the column. The buffer was eluted by gravity. The column was firstly washed using PBS buffer+10 mM of imidazole (10 column volumes) and secondly using PBS buffer+20 mM of imidazole. The ArsR protein was eluted using an imidazole gradient in PBS buffer (PBS buffer with increasing concentrations of imidazole: 30 to 400 mM). The fractions collected were analysed (SDS-PAGE gel). Fractions that contained the greatest quantity of protein were stored at 4° C. (3 ml of PBS buffer, imidazole 300 mM, pH 7.5). ArsR protein concentration was of 1 mg/ml. The protein is stable for 15 days at 4° C. It can be stored for several weeks at lower temperatures (−20 and −80° C.) in the presence of a cryoprotector (glycerol at 50%, volume/volume).

Example 6

Microplate Functionalization with a DNA Fragment Containing an ArsR Protein Binding Site In this example, the used DNA fragment containing the binding site of the ArsRFlagN-6His protein (SEQ ID NO. 22) is composed of a fragment of 41 biotinylated bases in position 5' (SEQ ID NO. 25, named "Pars2Lbio") hybridized to a further DNA fragment with 33 bases (SEQ ID NO 26, named "Pars2R"). The sequences Pars2Lbio and Pars2R were obtained by chemical synthesis (Eurofins MWG Operon, Ebersberg, Germany).

The biotinylated oligonucleotide ("Pars2Lbio") was used at a concentration of 1 to 10 nM. The complementary oligonucleotide ("Pars2R") was added in excess to enhance formation of the double strand. It was diluted in PBST buffer (between 1 and 10 nM, ideally 5, for the biotinylated oligonucleotide; between 4 and 40 nM, ideally 20, for the complementary oligonucleotide). The mixture was heated for one minute at 65° C. to eliminate any secondary structures that could have been formed by each oligonucleotide.

A "NUNC Immobilizer (trademark) Streptavidin" microplate (Nunc Streptavidin Microplate, Dominique Dutscher (ref. 056212), Brumath, France) with 96 wells with a useful volume of 100 µl each and whose surface is functionalized with streptavidin, was used. The wells in the microplate were washed three times using of 300 µl of PBST solution.

The DNA solution was then distributed in the microplate wells (100 µl per well). The microplate was placed at 25° C. for one hour to enable binding of the DNA fragments thanks to the biotin-streptavidin affinity.

Biotins and streptavidin show very strong affinity and are able to bind spontaneously. The presence of a biotin on the Opars1 sequence thus enabled the Opars1 sequence to bind to the surface of the wells functionalized with streptavidin.

The unbound DNA was eliminated by three successive washes using 300 µl of PBST per well.

The use of SEQ ID NO. 23 ("Pars1Lbio") and SEQ ID NO. 24 ("Pars1R"), instead of the respective sequences SEQ ID NO. 25 ("Pars2Lbio") and SEQ ID NO 26 ("Pars2R"), is also possible.

Example 7

Binding of an ArsRFlagN-6His Protein with the Pars2LRbio Sequence Functionalized on a Microplate 100 µl of PBSTLE solution were added in the microplate wells. The microplate was incubated for 60 minutes at 25° C. to enable non-specific binding of the milk proteins on the bottom and the walls of the well. This step limits non-specific binding of the ArsRFlagN-6His protein (SEQ ID NO. 22) and the conjugated anti-Flag antibodies (Ref. A9469, Sigma Aldrich, Saint-Quentin Fallavier, France). The unbound proteins were eliminated by three successive washes of the well using 300 µl of PBST buffer.

A solution of ArsRFlagN-6His protein (SEQ ID NO. 22) at 1 µg/ml was prepared in PBST buffer. 100 µl of this solution were added in each of the assay wells. The microplate was incubated for 60 minutes at 25° C., to enable the ArsRFlagN-6His proteins to bind with the DNA in the wells.

The unbound proteins were eliminated by three successive washes using 300 µl of PBST per well.

Example 8

Enzyme-Linked Immunosorbent Assay (ELISA) Method for Arsenic

The DNA fragment defined in example 6 and containing the ArsR protein binding site was bound to a support in the same way as presented in example 6 above.

A solution containing the ArsRFlagN-6His protein (SEQ ID NO. 22) was added according to the protocol presented in example 7 above, to enable the protein to bind with the DNA.

5 dilutions of arsenic solution, at 0 µg/L, 2 µg/L, 3 µg/L, 4 µg/L, and 5 µg/L respectively, were prepared in PBS to provide a control sample range. 100 µl of each of these dilutions were added respectively in a microplate well.

The microplate was incubated for 60 minutes at 25° C., to enable the arsenic to bind with the ArsRFlagN-6His proteins (SEQ ID NO. 22).

The unbound ArsRFlagN-6His proteins (SEQ ID NO. 22) were eliminated by three successive washed using 300 µl of PBST per well.

100 µl of a solution of anti-Flag antibody (Ref. A9469, Sigma Aldrich, Saint-Quentin Fallavier, France), conjugated with alkaline phosphatase, were added in each wells. The antibody was previously diluted in PBST in compliance with the supplier's recommendations (dilution factor 1/500). The microplate was incubated for 60 minutes at 25° C. to enable the antibody to bind with the ArsRFlagN-6His proteins.

The unbound anti-Flag antibodies were eliminated by three successive washes using 300 µl of PBST per well.

A CDP* solution at 0.25 mM was prepared in buffer 1. 100 µl of CDP* solution were placed in the different assay wells. The light emitted was immediately measured using a luminometer (LumiStar, BMG Lab Technologies).

The luminescence values (L) obtained are shown in table 4 below and illustrated by FIG. 4.

TABLE 4

Measurement of luminescence depending on arsenic concentration

| Concentration of AsIII (µM) | Concentration of AsIII (µg/L) | Luminescence value (L) | logL |
|---|---|---|---|
| 0 | 0 | 5,308 | 3.7249 |
| 0.027 | 2 | 4,710 | 3.6730 |
| 0.040 | 3 | 4,457 | 3.6490 |
| 0.053 | 4 | 4,061 | 3.6086 |
| 0.067 | 5 | 3,906 | 3.5917 |

The standard curve obtained is linear (FIG. 4), showing that the sensitivity of the technique is well below the detection limit of 10 µg/L for current methods.

Furthermore, the coefficient of determination $R^2=0.9981$, which is an indicator for judging the quality of a linear regression, confirms the reliability of the results observed.

Such results had never been obtained beforehand, especially as such low concentrations.

LISTS OF REFERENCES

[1] Bisson M., Houeix N., Hulot C., Lacroix G., Lefevre J. P., Leveque S., Magaud H., Morin A. 2006. Arsenic et ses dérivés inorganiques. INERIS-DRC-01-25590-00DF258.doc

[2] World Health Organization. 2006. Arsenic mitigation for safe groundwater. EB118/14.

[3] Hung D., Nekrassova O., Compton R. 2004. Analytical methods for inorganic arsenic in water: a review. Talanta 64:269-277.

[4] Mukhopadhyay R., Rosen B., Phung L., Silver S. 2002. Microbial arsenic: from geocycles to genes and enzymes. FEMS Microbiology Reviews 26:311-325.

[5] Sagiv J. (1980) Journal of the American Chemical Society, 102, 92

[6] J C Janson, L Ryden (1998). Protein purification: Principles, High-Resolution Methods, and Applications. Second edition, Wiley-VCH ISBN-10: 0-471-18626-0.

[7] Cordier-Ochsenbein, F., R. Guerois, et al. (1998). "Exploring the folding pathways of annexin I, a multidomain protein. II. Hierarchy in domain folding propensities may govern the folding process." J Mol Biol 279(5): 1177-85.

[8] Xu and Rosen (1997) Dimerization is essential for DNA binding and repression by the ArsR metalloregulatory protein of *Escherichia coli*. J. Biol. Chem., Vol. 272, No. 25, pp. 15734-15738.

[9] Fmoc Solid Phase Peptide Synthesis: A Practical Approach (Practical Approach Series) W. C. Chan (Editor), Peter D. White (Editor)", Oxford Univ Press 2000.

[10] ELISA, Methods in Molecular Biology, 1995, Volume 42, Part 1, 35-61, DOI: 10.1385/0-89603-279-5:35.

[11] Protocols for preparing immunogens, immunization of animals, and collection of antiserum may be found in *Antibodies: A Laboratory Manual*, E. Harlow and D. Lane, ed., Cold Spring Harbor Laboratory (Cold Spring Harbor, N.Y., 1988) pp. 55-120.

[12] The QiaExpressionist: A handbook for high-level expression and purification of 6×His-tagged proteins. June 2003. Fifth ed., Qiagen.

[13] Sorensen M A, Kurland C G, Pedersen S. (1989), Codon usage determines translation rate in *Escherichia coli*. J Mol. Biol. 1989; 207(2):365-77.

[14] Zhang S P, Zubay G, Goldman E., Low-usage codons in *Escherichia coli*, yeast, fruit fly and primates. Gene. 1991; 105(1):61-72.

[15] Rosenberg, A. H., Lade, B. N., Chui, D., Lin, S., Dunn, J. J., and Studier, F. W. (1987) Vectors for selective expression of cloned DNAs by T7 RNA polymerase. *Gene* 56 (1): 125-135

[16] Miroux and Walker, Over-production of proteins in *Escherichia coli*: mutant hosts that allow synthesis of some membrane proteins and globular proteins at high levels. J Mol. Biol. 1996; 260(3):289-98.

The invention claimed is:

1. A process for analyzing arsenic in a sample, comprising the following steps:
   (a) contacting a sample suspected of containing arsenic on a solid support functionalized with a DNA fragment comprising an ArsR protein binding site, site on which an ArsR protein is attached, the presence of arsenic causing separation of the ArsR protein from the DNA fragment;
   (b) incubation of the sample in contact with the said support;
   (c) elimination of ArsR protein separated from the DNA fragment by washing the support after the incubation carried out in step (b); and
   (d) analyzing by an ELISA technique to detect the presence or absence of ArsR protein remaining attached to the DNA fragment.

2. The process according to claim 1, said process further comprising a step (e) of comparison of the measurement made in step (d) with a control sample containing arsenic.

3. The process according to claim 1, wherein the functionalization of the DNA fragment on the solid support is achieved by streptavidin-biotin bond.

4. The process according to claim 1, wherein the incubation step (b) is carried out for a time period ranging from 1 minute to 90 minutes.

5. The process according to claim 1, wherein the incubation step (b) is carried out at a temperature ranging from 15° C. to 37° C.

6. The process according to claim 1, wherein the contacting step (a) is carried out with a buffer solution whose pH level is comprised between 6 and 8.

7. The process according to claim 1, wherein the DNA fragment containing an ArsR protein binding site is a promoter of the arsenic resistance gene of *E. coli*, or a part of the promoter of the arsenic resistance gene of *E. coli* enabling binding of an ArsR protein.

8. The process according to claim 1, wherein the sequence of the DNA fragment containing an ArsR protein binding site is SEQ ID NO. 1, SEQ ID NO. 17, SEQ ID NO. 23, SEQ ID NO. 24, SEQ ID NO. 25, SEQ ID NO. 26 or a sequence having at least 80% of identity with SEQ ID NO. 1, SEQ ID NO. 17, SEQ ID NO. 23, SEQ ID NO. 24, SEQ ID NO. 25 or SEQ ID NO. 26.

9. The process according to claim 1, wherein the solid support is made of polystyrene, polyethylene or polypropylene.

10. The process according to claim 1, wherein the ArsR protein is covalently bound to a known sequence of a recognition peptide, for the implementation of the ELISA test.

11. The process according to claim 10, wherein the sequence of the recognition peptide is selected from among SEQ ID NO. 10, SEQ ID NO. 11, SEQ ID NO. 12, SEQ ID NO. 13, SEQ ID NO. 14, SEQ ID NO. 15, SEQ ID NO. 16 and a sequence having at least 80% of identity with these sequences.

12. A kit intended for the detection of arsenic in a sample, said kit comprising:
   a solid support functionalizable or functionalized with a DNA fragment comprising an ArsR protein binding site;
   a DNA fragment containing an ArsR protein binding site;
   an ArsR protein;
   a means for detection by ELISA of the presence of the ArsR protein.

13. The kit according to claim 12, wherein the means for detection by ELISA of the presence of the ArsR protein, is a detection means using colorimetry or luminescence.

14. The kit according to claim 12, further comprising arsenic at a determined concentration.

15. The kit according to claim 12, wherein the solid support is a plate or a microplate containing a plurality of wells.

* * * * *

SEQUENCE LISTING

```
<160> NUMBER OF SEQ ID NOS: 26

<210> SEQ ID NO 1
<211> LENGTH: 254
<212> TYPE: DNA
<213> ORGANISM: Artificial Sequence
<220> FEATURE:
<223> OTHER INFORMATION: Opars1: operating region of the Escherichia
      coli ars operon

<400> SEQUENCE: 1
accaactcag ggctggaaag taaaaaaccg acgcaaagtc ggttttttta cgtcctgatt      60
cagacctcct ttcaaatgaa tagccaactc aaaattcaca cctattacct tcctctgcac    120
ttacacattc gttaagtcat atatgttttt gacttatccg cttcgaagag agacactacc    180
tgcaacaatc aggagcgcaa tatgtcattt ctgttaccca tccaattgtt caaaattctt    240
gctgatgaaa cccg                                                      254

<210> SEQ ID NO 2
<211> LENGTH: 19
<212> TYPE: DNA
<213> ORGANISM: Artificial Sequence
<220> FEATURE:
<223> OTHER INFORMATION: Opars1L primer

<400> SEQUENCE: 2
accaactcag ggctggaaa                                                   19

<210> SEQ ID NO 3
<211> LENGTH: 20
<212> TYPE: DNA
<213> ORGANISM: Artificial Sequence
<220> FEATURE:
<223> OTHER INFORMATION: Opars1R primer

<400> SEQUENCE: 3
cgggtttcat cagcaagaat                                                  20

<210> SEQ ID NO 4
<211> LENGTH: 117
<212> TYPE: PRT
<213> ORGANISM: Artificial Sequence
<220> FEATURE:
<223> OTHER INFORMATION: ArsR protein's sequence of Escherichia coli K12
      strain MG1655

<400> SEQUENCE: 4

Met Ser Phe Leu Leu Pro Ile Gln Leu Phe Lys Ile Leu Ala Asp Glu
1               5                   10                  15

Thr Arg Leu Gly Ile Val Leu Leu Ser Glu Leu Gly Glu Leu Cys
            20                  25                  30

Val Cys Asp Leu Cys Thr Ala Leu Asp Gln Ser Gln Pro Lys Ile Ser
        35                  40                  45

Arg His Leu Ala Leu Leu Arg Glu Ser Gly Leu Leu Leu Asp Arg Lys
    50                  55                  60

Gln Gly Lys Trp Val His Tyr Arg Leu Ser Pro His Ile Pro Ala Trp
65                  70                  75                  80
```

Ala Ala Lys Ile Ile Asp Glu Ala Trp Arg Cys Glu Gln Glu Lys Val
            85                  90                  95

Gln Ala Ile Val Arg Asn Leu Ala Arg Gln Asn Cys Ser Gly Asp Ser
        100                 105                 110

Lys Asn Ile Cys Ser
        115

<210> SEQ ID NO 5
<211> LENGTH: 384
<212> TYPE: DNA
<213> ORGANISM: Artificial Sequence
<220> FEATURE:
<223> OTHER INFORMATION: arsR gene's sequence of Escherichia coli K12
      strain MG1655

<400> SEQUENCE: 5
atgcttgatt ataaagatga tgatgataaa ggctcatttc tgttacccat ccaattgttc      60
aaaattcttg ctgatgaaac ccgtctgggc atcgttttac tgctcagcga actgggagag     120
ttatgcgtct gcgatctctg cactgctctc gaccagtcgc agcccaagat ctcccgccac     180
ctggcattgc tgcgtgaaag cgggctattg ctggaccgca agcaaggtaa gtgggttcat     240
taccgcttat caccgcatat tccagcatgg gcggcgaaaa ttattgatga ggcctggcga     300
tgtgaacagg aaaaggttca ggcgattgtc cgcaacctgg ctcgacaaaa ctgttccggg     360
gacagtaaga acatttgcag ttaa                                            384

<210> SEQ ID NO 6
<211> LENGTH: 61
<212> TYPE: DNA
<213> ORGANISM: Artificial Sequence
<220> FEATURE:
<223> OTHER INFORMATION: arsRR primer

<400> SEQUENCE: 6
cttggatcct tagcctttat catcatcatc tttataatca ctgcaaatgt tcttactgtc      60
c                                                                      61

<210> SEQ ID NO 7
<211> LENGTH: 59
<212> TYPE: DNA
<213> ORGANISM: Artificial Sequence
<220> FEATURE:
<223> OTHER INFORMATION: arsRL primer

<400> SEQUENCE: 7
ctagcatgct tgattataaa gatgatgatg ataaaggctc atttctgtta cccatccaa       59

<210> SEQ ID NO 8
<211> LENGTH: 381
<212> TYPE: DNA
<213> ORGANISM: Artificial Sequence
<220> FEATURE:
<223> OTHER INFORMATION: arsR gene's sequence of the of Escherichia
      coli K12 strain MG1655 in which the sequence coding for the Flag
      peptide has been inserted in N-terminal position, downstream from
      the ATG initiation codon

<400> SEQUENCE: 8
atggattata aagatgatga tgataaaggc tcatttctgt tacccatcca attgttcaaa      60
attcttgctg atgaaacccg tctgggcatc gttttactgc tcagcgaact gggagagtta    120
tgcgtctgcg atctctgcac tgctctcgac cagtcgcagc ccaagatctc ccgccacctg    180

```
gcattgctgc gtgaaagcgg gctattgctg gaccgcaagc aaggtaagtg ggttcattac    240
cgcttatcac cgcatattcc agcatgggcg gcgaaaatta ttgatgaggc ctggcgatgt    300
gaacaggaaa aggttcaggc gattgtccgc aacctggctc gacaaaactg ttccggggac    360
agtaagaaca tttgcagtta a                                              381
```

```
<210> SEQ ID NO 9
<211> LENGTH: 127
<212> TYPE: PRT
<213> ORGANISM: Artificial Sequence
<220> FEATURE:
<223> OTHER INFORMATION: ArsRFlagN protein's sequence

<400> SEQUENCE: 9
```

Met Leu Asp Tyr Lys Asp Asp Asp Lys Gly Ser Phe Leu Leu Pro
1               5                   10                  15

Ile Gln Leu Phe Lys Ile Leu Ala Asp Glu Thr Arg Leu Gly Ile Val
            20                  25                  30

Leu Leu Leu Ser Glu Leu Gly Glu Leu Cys Val Cys Asp Leu Cys Thr
        35                  40                  45

Ala Leu Asp Gln Ser Gln Pro Lys Ile Ser Arg His Leu Ala Leu Leu
    50                  55                  60

Arg Glu Ser Gly Leu Leu Leu Asp Arg Lys Gln Gly Lys Trp Val His
65                  70                  75                  80

Tyr Arg Leu Ser Pro His Ile Pro Ala Trp Ala Ala Lys Ile Ile Asp
                85                  90                  95

Glu Ala Trp Arg Cys Glu Gln Glu Lys Val Gln Ala Ile Val Arg Asn
            100                 105                 110

Leu Ala Arg Gln Asn Cys Ser Gly Asp Ser Lys Asn Ile Cys Ser
        115                 120                 125

```
<210> SEQ ID NO 10
<211> LENGTH: 9
<212> TYPE: PRT
<213> ORGANISM: Artificial Sequence
<220> FEATURE:
<223> OTHER INFORMATION: Recognition peptide: Flag

<400> SEQUENCE: 10
```

Asp Tyr Lys Asp Asp Asp Asp Lys Gly
1               5

```
<210> SEQ ID NO 11
<211> LENGTH: 14
<212> TYPE: PRT
<213> ORGANISM: Artificial Sequence
<220> FEATURE:
<223> OTHER INFORMATION: Recognition peptide: peptide V5

<400> SEQUENCE: 11
```

Gly Lys Pro Ile Pro Asn Pro Leu Leu Gly Leu Asp Ser Thr
1               5                   10

```
<210> SEQ ID NO 12
<211> LENGTH: 6
<212> TYPE: PRT
<213> ORGANISM: Artificial Sequence
<220> FEATURE:
<223> OTHER INFORMATION: Recognition peptide: His

<400> SEQUENCE: 12
```

His His His His His His

<210> SEQ ID NO 13
<211> LENGTH: 10
<212> TYPE: PRT
<213> ORGANISM: Artificial Sequence
<220> FEATURE:
<223> OTHER INFORMATION: Recognition peptide: c-MYC

<400> SEQUENCE: 13

Glu Gln Lys Leu Ile Ser Glu Glu Asp Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Recognition peptide: HA

<400> SEQUENCE: 14

Tyr Pro Tyr Asp Val Pro Asp Tyr Ala
1               5

<210> SEQ ID NO 15
<211> LENGTH: 11
<212> TYPE: PRT
<213> ORGANISM: Artificial Sequence
<220> FEATURE:
<223> OTHER INFORMATION: Recognition peptide: VSV-G

<400> SEQUENCE: 15

Tyr Thr Asp Ile Glu Met Asn Arg Leu Gly Lys
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Recognition peptide: AU5

<400> SEQUENCE: 16

Thr Asp Phe Tyr Leu Lys
1               5

<210> SEQ ID NO 17
<211> LENGTH: 127
<212> TYPE: DNA
<213> ORGANISM: Artificial Sequence
<220> FEATURE:
<223> OTHER INFORMATION: E. coli R-factor R773 arsR gene (X16045)

<400> SEQUENCE: 17
gaattccaag ttatctcacc taccttaagg taatagtgtg attaatcata tgcgtttttg        60
gttatgtgtt gtttgactta atatcagagc cgagagatac ttgttttcta caaaggagag       120
ggaaatg                                                                 127

<210> SEQ ID NO 18
<211> LENGTH: 380
<212> TYPE: DNA
<213> ORGANISM: Artificial Sequence
<220> FEATURE:
<223> OTHER INFORMATION: DNAc coding for optimized ArsRFlagN

<400> SEQUENCE: 18

```
ccatggacta caaagacgac gacgacaaag gtagctttct gctgccgatc cagctgttca    60
aaattctggc agacgaaacc cgtctgggta ttgtgttact gctgagcgaa ttaggcgaac   120
tgtgcgtttg cgatctgtgt accgcgttag atcagagtca gccgaaaatt agccgtcatc   180
tggcgttatt acgcgaaagc ggtctgttac tggaccgtaa acagggcaaa tgggtccatt   240
accgcttatc tccgcatatt ccggcttggg cagcaaaaat cattgacgaa gcctggcgtt   300
gcgaacagga aaaagttcag gcgatcgtcc gtaacctggc acgtcaaaat tgtagcggcg   360
atagcaaaaa catctcgagc                                               380
```

```
<210> SEQ ID NO 19
<211> LENGTH: 24
<212> TYPE: DNA
<213> ORGANISM: Artificial Sequence
<220> FEATURE:
<223> OTHER INFORMATION: Tag sequence

<400> SEQUENCE: 19
gactacaaag acgacgacga caaa                                           24

<210> SEQ ID NO 20
<211> LENGTH: 345
<212> TYPE: DNA
<213> ORGANISM: Artificial Sequence
<220> FEATURE:
<223> OTHER INFORMATION: Optimized sequence of the arsR gene

<400> SEQUENCE: 20
```

```
ggtagctttc tgctgccgat ccagctgttc aaaattctgg cagacgaaac ccgtctgggt    60
attgtgttac tgctgagcga attaggcgaa ctgtgcgttt gcgatctgtg taccgcgtta   120
gatcagagtc agccgaaaat tagccgtcat ctggcgttat tacgcgaaag cggtctgtta   180
ctggaccgta aacagggcaa atgggtccat taccgcttat ctccgcatat tccggcttgg   240
gcagcaaaaa tcattgacga agcctggcgt tgcgaacagg aaaaagttca ggcgatcgtc   300
cgtaacctgg cacgtcaaaa ttgtagcggc gatagcaaaa acatc                   345
```

```
<210> SEQ ID NO 21
<211> LENGTH: 399
<212> TYPE: DNA
<213> ORGANISM: Artificial Sequence
<220> FEATURE:
<223> OTHER INFORMATION: ADNc of ArsRFlagN-6His

<400> SEQUENCE: 21
```

```
atggactaca agacgacgac gacaaaggt agctttctgc tgccgatcca gctgttcaaa    60
attctggcag acgaaacccg tctgggtatt gtgttactgc tgagcgaatt aggcgaactg   120
tgcgtttgcg atctgtgtac cgcgttagat cagagtcagc cgaaaattag ccgtcatctg   180
gcgttattac gcgaaagcgg tctgttactg gaccgtaaac agggcaaatg gtccattac   240 cgcttatctc cgcatattcc ggcttgggca gcaaaaatca ttgacgaagc ctggcgttgc   300
gaacaggaaa agttcaggc gatcgtccgt aacctggcac gtcaaaattg tagcggcgat   360
agcaaaaaca tctcgagcca ccaccaccac caccactga                          399
```

```
<210> SEQ ID NO 22
<211> LENGTH: 132
<212> TYPE: PRT
<213> ORGANISM: Artificial Sequence
<220> FEATURE:
```

<223> OTHER INFORMATION: ArsRFlagN-6His protein

<400> SEQUENCE: 22

Met Asp Tyr Lys Asp Asp Asp Lys Gly Ser Phe Leu Leu Pro Ile
1               5                   10                  15

Gln Leu Phe Lys Ile Leu Ala Asp Glu Thr Arg Leu Gly Ile Val Leu
            20                  25                  30

Leu Leu Ser Glu Leu Gly Glu Leu Cys Val Cys Asp Leu Cys Thr Ala
        35                  40                  45

Leu Asp Gln Ser Gln Pro Lys Ile Ser Arg His Leu Ala Leu Leu Arg
    50                  55                  60

Glu Ser Gly Leu Leu Leu Asp Arg Lys Gln Gly Lys Trp Val His Tyr
65                  70                  75                  80

Arg Leu Ser Pro His Ile Pro Ala Trp Ala Ala Lys Ile Ile Asp Glu
                85                  90                  95

Ala Trp Arg Cys Glu Gln Glu Lys Val Gln Ala Ile Val Arg Asn Leu
            100                 105                 110

Ala Arg Gln Asn Cys Ser Gly Asp Ser Lys Asn Ile Ser Ser His His
        115                 120                 125

His His His His
    130

<210> SEQ ID NO 23
<211> LENGTH: 41
<212> TYPE: DNA
<213> ORGANISM: Artificial Sequence
<220> FEATURE:
<223> OTHER INFORMATION: Sequence fixing biotinylated ArsR Pars1L

<400> SEQUENCE: 23
ctgcacttac acattcgtta agtcatatat gtttttgact t                41

<210> SEQ ID NO 24
<211> LENGTH: 39
<212> TYPE: DNA
<213> ORGANISM: Artificial Sequence
<220> FEATURE:
<223> OTHER INFORMATION: Sequence fixing ArsR Pars1R

<400> SEQUENCE: 24
aagtcaaaaa catatatgac ttaacgaatg tgtaagtgc                  39

<210> SEQ ID NO 25
<211> LENGTH: 41
<212> TYPE: DNA
<213> ORGANISM: Artificial Sequence
<220> FEATURE:
<223> OTHER INFORMATION: Sequence fixing biotinylated ArsR Pars2L

<400> SEQUENCE: 25 tttttttgc gcattcgtta agtcatatat gtttttgact t                41

<210> SEQ ID NO 26
<211> LENGTH: 33
<212> TYPE: DNA
<213> ORGANISM: Artificial Sequence
<220> FEATURE:
<223> OTHER INFORMATION: Sequence fixing ArsR Pars2R

<400> SEQUENCE: 26
aagtcaaaaa catatatgac ttaacgaatc ccc                        33